United States Patent [19]

Palomo Coll

[11] 4,058,660
[45] Nov. 15, 1977

[54] PROCESS FOR THE CONVERSION OF 6-AMINOPENICILLANIC ACID (6-APA) IN 7-AMINODESACETOXYCEPHALOSPO-RANIC ACID (7-ADCA)

[76] Inventor: Antonio Luis Palomo Coll, Maestro Perez Cabrero 7, Barcelona, Spain

[21] Appl. No.: 627,468

[22] Filed: Oct. 30, 1975

[30] Foreign Application Priority Data

Nov. 2, 1974 Spain .................................. 431585

[51] Int. Cl.$^2$ .......................................... C07D 501/10
[52] U.S. Cl. .................................................. 544/18
[58] Field of Search .................................. 260/243 C

[56] References Cited

U.S. PATENT DOCUMENTS

| 3,766,177 | 10/1973 | Webber et al. | 260/243 C |
| 3,879,398 | 4/1975 | Ellerton et al. | 260/243 C |
| 3,932,387 | 1/1976 | Kukolja et al. | 260/243 C |
| 3,932,398 | 1/1976 | Nudelman et al. | 260/243 C |
| 3,947,465 | 3/1976 | Coll | 260/243 C |
| 3,953,440 | 4/1976 | Hatfield | 260/243 C |

Primary Examiner—Nicholas S. Rizzo
Assistant Examiner—James H. Turnipseed

[57] ABSTRACT

A process consisting in reacting one mole of an alpha-halobenzyl penicillin-(s)-sulphoxide with at least two moles of 3-trimethylsilyl-2-oxazolidinone (TMSO) at a temperature of between 60 and 120° C in acetonitrile solution in the presence of a tertiary organic base p-toluene sulphonate and thiourea is described. The solvent is removed by evaporation from the solution obtained, the residue is diluted with water, the pH is adjusted to 4.2 and 7-aminodesacetoxycephalosporanic acid (7-ADCA) is isolated 2 Claims, No Drawings

PROCESS FOR THE CONVERSION OF 6-AMINOPENICILLANIC ACID (6-APA) IN 7-AMINODESACETOXYCEPHALOSPORANIC ACID (7-ADCA)

FIELD OF THE INVENTION

This invention relates to a process for the conversion of 6-aminopenicillanic acid (6-APA) to 7-aminodesacetoxycephalosporanic acid (7-ADCA).

The conversion of 6-APA to 7-ADCA takes place through the acylation of 6-APA and oxidation of the sulphur atom to produce alpha-chlorobenzyl penicillin-(s)-sulphoxide through the application of normal techniques, whereas the cycloexpansion of the thiazoline nucleus to thiazine and unblocking to form 7-ADCA is effected in a single process as shown in Reaction Scheme I.

REACTION SCHEME I

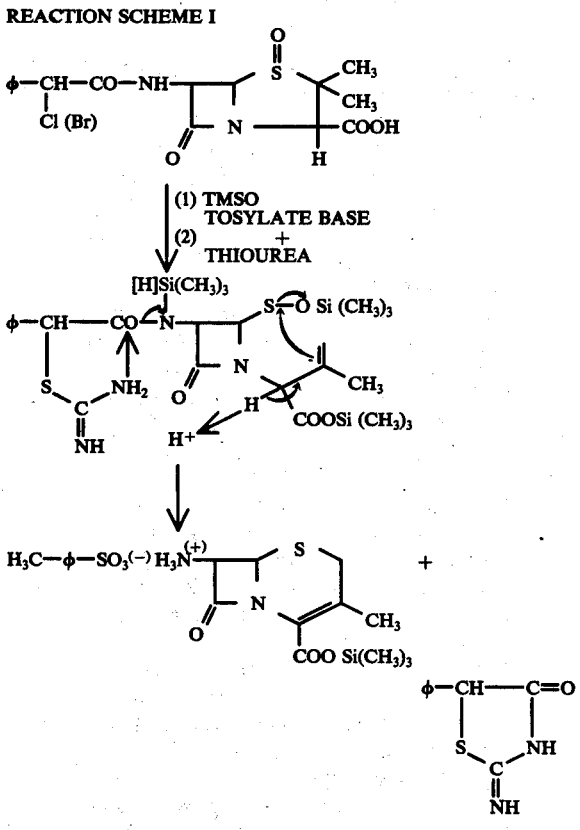

The process is equally applicable both if 6-APA or epi-6-APA are used, namely, with the epimers beta-6-APA and alpha-6-APA to obtain the corresponding epimers of 7-ADCA, with a C-6 epimer of alpha-chlorobenzyl penicillin-(s)-sulphoxide being used as starting material.

DESCRIPTION OF PRIOR ART

It is known that 7-chloroacetamidocephalosporanic acid undergoes spontaneous deacylation with thiourea to form 7-aminocephalosporanic acid (7-ACA) and that this type of reaction with chloroacetamides has been generalised by Masaki et al. Similarly, the production of 6-APA should be expected with chloromethylpenicillin (E.H. Flyn. Cephalosporins and Penicillins, Chemistry and Biology; Academic Press, New York 1972, p. 69).

To unblock (deacylate) for the production of 6-APA-(s)-sulphoxide, the corresponding alpha-chlorobenzyl penicillin was made to react with 3-trimethylsilyl-silylate -oxazolidinone (TMSO) to silylate the carboxyl and amide groups. The process was then continued by reacting with thiourea in acetonitrile. The result was surprising, since 7-ADCA and not the expected compound was isolated.

It is known that the cycloexpansion of a penicillin-(s)-sulphoxide is effected with acid anhydrides in the presence of sulphonic acids (Morin et al., U.S. Pat. 3,275,626); with chlorosilanes (Sp. Pat. No. 388.733, British patent application 7.892/70 and 35,797/70) cognated, now Brit. Pat. No. 1,355,791 in the presence of organic bases; with trimethylchlorosilane in similar conditions (British Pat. 763.104) and with sulphonic acids (Sp. Pat. No. 388,964; U.S. Ser. No. 16,929, filed Mar. 5, 1970, now U.S. Pat. No. 3,674,775.

Spanish Pat. No. 411.867, (U.S. Ser. No. 443.849, filed Feb. 19, 1974, now U.S. Pat. No. 3,947,465) also describes that 3-methylsilyl-2-oxazolidinone (TMSO) is a powerful silylating agent which acts via basic catalysis, namely, or the nucleophilic groups which, in the case of alpha-chlorobenzyl penicillin-(s)-sulphoxide, provides the carboxylate ion, in the presence of tertiary organic bases, whilst the silylation of the amide group is effected by heating of the reaction mixture.

SUMMARY OF THE INVENTION

It has now been discovered that through silylation TMSO also picks up the intermediate sulphonic acid produced by the mechanism proposed by Morin et al. (J. Am. Chem. Soc., 85, 1896, 1963) and, by reaction with thiourea in the presence of tertiary base tosylates, the pseudothiourea intermediate represented by Reaction Scheme I is produced. This evolves rapidly to the reaction products, phenylpseudothiohydantoin and 7-ADCA tosylate.

Acylation with TMSO implies the presence of tertiary bases, as disclosed in Spanish Pat. No. 411.867. The later addition of p-toluene sulphonic acid is necessary to avoid the destructive action of the base on the pseudothiourea compound. It is observed that the presence of the tosylates facilitates the cyclisation for formation of the thiazine nucleus.

According to Reaction Scheme I, for the purposes of the invention, one convenient way consists of heating a solution of the acid form of alpha-chlorobenzyl penicillin-(s)sulphoxide in acetonitrile under reflux for 30–60 minutes, with at least 2 moles of TMSO per mole of penicillin, in the presence of a small amount, for example, up to 0.1 mole of triethylamine tosylate, and then in the presence of 1 mole of a tertiary base tosylate and from 1 to 1.2 mole of thiourea.

A further method is to add 1 mole of tertiary organic base to the solution of the acid form of 1 mole of penicillin-(s)-sulphoxide, to provide the salt of the corresponding penicillin. Then, at least 2 moles of TMSO are added with stirring at room temperature. After 15 to 30 minutes, the base released is neutralised by addition of anhydrous p-toluene sulphonic acid and thiourea, by heating under reflux for 60 to 120 minutes. In either case, the isolation of the 7-ADCA is effected by concentration of the solution and dilution with water, thereby producing hydrolysis of the silyl ester. The phenylpseudohydantoin is removed by filtration and the pH is adjusted to precipitate the 7-ADCA out.

Tosylates suited to the invention are the p-toluene sulphonates of triethylamine, quinaline and picolines, with the reaction being perfomed in non-hydrolylic solvents such as benzene, toluene, chloroform, dimethylformamide, dimethylacetamide and 1,2-dimethoxyethane. As well as acetonitrile, other preferred solvents are dimethylacetamide and blends thereof with other solvents.

All attempts to isolate the intermediate compound shown in Reaction Scheme I, as the possible intermediates of alpha-pseudothiourea benzyl penicillin-(s)-sulphoxide and 7(alpha-pseudothiourea-phenylacetamido) desacetoxycephalosporanic acid, failed, since the conversion speed into 7-ADCA is much higher than the speed of accumulation of the intermediate. Thus, it was observed from the reaction of 7(alpha-chlorophenylacetamido) desacetoxycephalosporanic acid silyl ester with thiourea that the presence of the intermediate was not detected, whereas 7-ADCA is isolated and the conversion or deacylation speed increases when the amide nitrogen is previously silylated, 2 moles of TMSO per mole of cephalosporin being necessary.

The same results are obtained when alpha-bromophenylacetic acid replaces the alpha-chlorophenylacetic acid in the acylation of the 6-APA.

DETAILED DESCRIPTION OF THE INVENTION

EXAMPLE I

A solution of 0.1 mole of alpha-chlorobenzylpenicillin-(s)-sulphoxide sodium salt (40.57g) was adjusted to pH 2 and extracted with methylene chloride, dried with anhydrous sodium sulphate and evaporated at reduced pressure. The residue was dissolved in 250 ml of acetonitrile.

To the above solution, there were added 0.28 mole of 3-trimethylsilyl-2-oxazolidinone (TMSO, 38.2 ml) and 0.02 mole of triethylamine p-toluenesulphonate (8.468 g). After stirring for 15 minutes, the mixture was heated under reflux for 120 minutes. Thereafter 0.1 mole of dimethylaniline p-toluene sulphonate (29.3 g) and 0.12 mole of thiourea (9.13 g) were added and heating was maintained for a further 60 minutes. Thereafter the mixture was concentrated at reduced pressure and water (100 ml) was added to the residue. The pH was adjusted to 8.5 in the presence of methylene chloride, the phenyl-pseudothio-hydantoin was filtered out and the water phase was decanted off. After further adjustment To pH 4.2, the mixture was filtered again to give 7-ADCA (14.9 g) with 70% yield. Identified by its IR spectrum, m.p. 232–42 (d) and $[\alpha]_D^{20}$= 105.0° (C=1%, 0.5 N HCL).

EXAMPLES II

The pH of an aqueous solution of 0.1 mole (38.87 g) of alpha-chlorobenzyl desacetoxycephalosporin sodium salt was adjusted to 1.5 and the solution was extracted with chloroform (100 ml). 0.12 mole (18.4 ml) of TMSO and 0.01 mole (1.4 ml) of triethylamine were added to the dry solution, wth stirring for 15 minutes at room temperature. Thereafter dimethylacetamide (150 ml) and thiourea (9.13 g) were added, the mixture was heated under reflux for 60 minutes, followed by cooling, addition of 100 ml water and hydrochloric acid to an acid pH. The solution was filtered, the organic phase was drawn off and the aqueous liquors were extracted with more chloroform. The water phase was treated as in Example I. The precipitate was filtered, washed with water, acetone an dried to give 7-ADCA (16 g), with a yield of 75%, m.p. 230–42(d) and $[\alpha]_D^{20} = +104.8°$ (0.5N HCL).

EXAMPLE III

Following Example I and replacing the alpha-chloro derivative with alpha-bromobenzyl penicillin-(s)-sulphoxide (0.2 mole, 45.0 g), 7-ADCA was obtained with a similar yield. Identified by its IR spectrum, m.p. and optical activity.

EXAMPLE IV

Following Example I and replacing the alpha-chloro derivative with epi-alpha-chlorobenzyl penicillin-(s)-sulphoxide, epi-7-ADCA was obtained with a similar yield and with $[\alpha]_D^{20} = +203.6°$ (C = 1%, 0.5N HCL) ) and m.p. 238–42 (d).

EXAMPLE V

Following Example I, with 0.1 mole alpha-chlorobenzyl penicillin-(s)-sulphoxide, acid form, and replacing the acetonitrile with dimethylformamide and the dimethylaniline p-toluene sulphonate with the equivalet amount of alpha-picoline p-toluene sulphonate, 7-ADCA was obtained with a similar yield.

EXAMPLE VI

Following Example I, wth 0.1 mole of alpha-chlorophenyl penicillin, acid form, and replacing the acetonitrile with one half of chloroform and then adding one half of acetonitrile and beta-picoline p-toluene sulphonate, instead of diethylaniline p-toluene sulphonate, 7-ADCA was obtained, with a similar yield.

EXAMPLE VII

Following example I, with 0.1 mole of alpha-bromophenyl penicillin and replacing the acetonitrile with 1,2-dimethoxyethane and the dimethylaniline p-toluene sulphonate with gamma-picoline p-toluene sulphonate, 7-ADCA was obtained, with a similar yield.

What I claim is:

1. In the process for the conversion of 6-aminopenicillanic acid (6-APA) to 7-aminodesacetoxycephalosporanic acid (7-ACDA), the improvement comprises reacting one mole of a compound selected from the group consisting of 2-chloro- and 2-bromobenzyl penicillin-(s)-sulphoxide with from two to four moles of 3-trimethylsilyl-2-oxazolidinone (TMSO) at a temperature of between 60° and 120° C in an inert non-hydroxylic solvent and in the presence of thiourea and a compound selected from the group consisting of triethylamine dimethylaniline, quinoline and picoline p-toluene sulfonate to obtain a solution, thereafter removing the solvent by evaporation, diluting the residue with water, adjusting the pH to 4.2, and isolating 7-aminodesacetoxycephalosporanic acid (7-ADCA).

2. The process of claim 1, wherein the non-hydroxylic solvent is selected from the group consisting of acetonitrile, benzene, toluene, chloroform, 1,2-dimethoxyethane, dimethylformamide and dimethylacetamide and a mixture of dimethylacetamide with at least one other of the recited solvents.

* * * * *